United States Patent
Kim et al.

(10) Patent No.: US 11,071,748 B2
(45) Date of Patent: Jul. 27, 2021

(54) USE OF CADPR OR NAADP ANTAGONISTS

(71) Applicant: Industrial Cooperation Foundation Chonbuk National University, Jeollabuk-do (KR)

(72) Inventors: Uh Hyun Kim, Jeollabuk-do (KR); Dae Ryoung Park, Jeollabuk-do (KR); Kwang Hyun Park, Jeollabuk-do (KR)

(73) Assignee: Industrial Cooperation Foundation Chonbuk National University, Joellabuk-do (KR)

( * ) Notice: Subject to any disclaimer, the term of this patent is extended or adjusted under 35 U.S.C. 154(b) by 0 days.

(21) Appl. No.: 16/340,639

(22) PCT Filed: Oct. 11, 2017

(86) PCT No.: PCT/KR2017/011181
§ 371 (c)(1),
(2) Date: Apr. 9, 2019

(87) PCT Pub. No.: WO2018/070774
PCT Pub. Date: Apr. 19, 2018

(65) Prior Publication Data
US 2020/0046750 A1 Feb. 13, 2020

(30) Foreign Application Priority Data

Oct. 11, 2016 (KR) .......................... 10-2016-131366
Oct. 11, 2016 (KR) .......................... 10-2016-131468

(51) Int. Cl.
| | |
|---|---|
| *A61K 31/496* | (2006.01) |
| *A61P 21/00* | (2006.01) |
| *A61K 31/7076* | (2006.01) |
| *A61P 17/02* | (2006.01) |
| *A61K 9/00* | (2006.01) |

(52) U.S. Cl.
CPC ........ *A61K 31/7076* (2013.01); *A61K 9/0014* (2013.01); *A61K 31/496* (2013.01); *A61P 17/02* (2018.01); *A61P 21/00* (2018.01)

(58) Field of Classification Search
None
See application file for complete search history.

(56) References Cited

FOREIGN PATENT DOCUMENTS

WO    WO-2017142368 A2 *  8/2017

* cited by examiner

*Primary Examiner* — Traviss C McIntosh, III
(74) *Attorney, Agent, or Firm* — Wood, Phillips, Katz, Clark & Mortimer (57) ABSTRACT

When using a pharmaceutical composition for preventing or treating malignant hyperthermia, containing NAADP antagonists, of the present invention, malignant hyperthermia can be effectively prevented or treated through the inhibition of an oxygen consumption rate abnormal increase, which is associated with a ryanodine receptor (RYR) of skeletal muscles. In addition, the present invention can be used even after the onset of malignant hyperthermia and can inhibit an oxygen consumption rate abnormal increase even at concentrations lower than those of conventional agents for treating malignant hyperthermia, thereby enabling conventional agents for treating malignant hyperthermia to be replaced, and can be stably used, thereby being effectively usable in relevant industries. Furthermore, when using a skin regenerating composition, containing cADPR or NAADP antagonists, of the present invention, the skin can be protected from skin cell damage caused by UV-B of ultraviolet rays, and the skin regenerating composition has an excellent ability to recover and regenerate damaged skin and has no side effects on the same, thereby being usable in various forms such as a skin external preparation, a pharmaceutical composition, a cosmetic composition, and a food composition.

4 Claims, 4 Drawing Sheets

USE OF CADPR OR NAADP ANTAGONISTS

TECHNICAL FIELD

The present invention relates to a pharmaceutical composition for preventing or treating malignant hyperthermia including an NAADP antagonist.

The present invention also relates to a skin regenerating composition comprising a cADPR or NAADP antagonist.

BACKGROUND ART

Malignant hyperthermia is a disease that occurs when using anesthetics, particularly inhalation-type anesthetics (halothane, isoflurane, etc.) and succinylcholine-type anesthetics during surgery and occurs in patients with a genetic disorder in the ryanodine receptor (RYR) in the skeletal muscle. This disease leads to death due to the body temperature increase caused by increasing in the irreversible oxygen consumption rate of the human skeletal muscle. The malignant hyperthermia is a disease that occurs in one person per about one hundred thousand persons, and many cases have been reported all over the world. Dantrolene, the RYR inhibitor, is currently used clinically as the only medication, but the poor water solubility of the drug leads to limitations that large amounts of medication are required. Further, the prognosis has been reported to be poor, and thus it is urgent to develop therapeutic agents for malignant hyperthermia.

In general, there are two kinds of skin aging phenomenon such as natural aging which starts from 25 to 26 years old and photoaging or exogenous aging by ultraviolet rays. Photoaging or exogenous aging refers to aging that occurs when the skin is always exposed to the external environment. It is difficult to maintain the proper moisture of the skin due to the dry indoor environment caused by the use of cooling and heating devices, and it is difficult for the skin to maintain normal moisture by the wind and chemicals etc. In particular, since exogenous aging is mainly caused by exposure to ultraviolet rays, if one is careful, it can be avoided considerably. This is a big difference from endogenous aging. The primary cause of this photoaging is known as active oxygen generated when sunlight (ultraviolet rays) is received. The ultraviolet rays contained in the sunlight can be divided into UV-C, UV-B and UV-A according to the wavelength range.

The UV-A (ranging from 320 nm to 400 nm) is not absorbed by the ozone layer but has a wavelength range of 320 nm to 400 nm (ranging from 0.32 µm to 0.40 µm). The UV-A has less energy than UV-B, but it can blacken the skin.

The UV-B is a major UV area that burns skin, but the UV-A not only makes the skin red but also acts on the skin's immune system and thus causes long-term skin damage due to skin aging.

The UV-B (ranging from 280 nm to 320 nm) is mostly absorbed by the ozone layer, but some reaches the surface of the earth. The UV-B, which reaches the earth in a very small amount, corresponds to the wavelength range of 0.28 µm to 0.32 µm. The UV-B can burn the skin of animals including human and can penetrate skin tissue to induce skin damage. The UV-B is sometimes considered to be a cause of skin cancer. Most of the causes of the skin cancer have been reported to be associated with exposure to sunlight and UV-B. Meanwhile, the UV-B is an important factor in the body as it activates pro-vitamin D in the skin to be converted into vitamin D, which is essential for the human body.

The UV-C (ranging from 100 nm to 280 nm) is entirely absorbed by the ozone layer and has a wavelength range of 0.20 µm to 0.29 µm, having a detrimental effect on life such as causing chromosomal variations, killing single cell organisms, and damaging the cornea of the eyes.

Accordingly, there is a need to develop a drug that protects and restores skin cell damage induced by UV-B, a wavelength region that causes major skin damage.

Meanwhile, cADPR and NAADP are known to induce the release of $Ca^{2+}$ ions from the endoplasmic reticulum, and their antagonists act competitively with them and inhibit their function. So far, their use for skin regeneration has not been known although many of the actions of these cADPR and NAADP antagonists are known.

DISCLOSURE

Technical Problem

It has been reported that Dantrolene, a conventional therapeutic agent for malignant hyperthermia, requires a large amount of drug due to its low water solubility, and its prognosis is also poor.

Accordingly, the purpose of the present invention is to provide a novel pharmaceutical composition for preventing or treating malignant hyperthermia.

Further, the purpose of the present invention is to provide a pharmaceutical composition for preventing or treating malignant hyperthermia comprising an NAADP antagonist.

Further, the purpose of the present invention is to provide a skin regenerating composition comprising a cADPR antagonist and/or a NAADP antagonist.

Further, the purpose of the present invention is to provide a skin external preparation, a skin disease-treating pharmaceutical composition, a cosmetic composition, and a food composition comprising the skin regenerating composition.

Technical Solution

In order to solve the above problems, the present invention provides a pharmaceutical composition for preventing or treating malignant hyperthermia comprising an NAADP antagonist.

1. A pharmaceutical composition for preventing or treating malignant hyperthermia, the pharmaceutical composition comprising a compound represented by the following chemical formula 1:

[Chemical Formula 1]

wherein X is halogen, and R is OH or $OC_{1-5}$ alkyl.

Further, the inventors of the present invention have found that cADPR and NAADP antagonists can promote skin regeneration, thereby completing the present invention. Therefore, means for solving the above problems are as follows.

2. A skin regenerating composition comprising at least one compounds selected from the group consisting of a compound represented by the following chemical formula 1 and a compound represented by the following chemical formula 2:

[Chemical Formula 1]

[Chemical Formula 2]

wherein A is halogen, $NH_2$, $OC_{1-5}$ alkyl group or $C_{1-5}$ alkyl group; X is halogen, and R is OH or $OC_{1-5}$ alkyl.

3. A skin external preparation comprising the skin regenerating composition of clause 2.

4. A skin disease-treating pharmaceutical composition comprising the skin regenerating composition of clause 2.

5. A cosmetic composition comprising the skin regenerating composition of clause 2.

6. A food composition comprising the skin regenerating composition of clause 2.

Advantageous Effects

When using a pharmaceutical composition for preventing or treating malignant hyperthermia comprising NAADP antagonists of the present invention, irreversible oxygen consumption rate can be reduced in the skeletal muscle of patients with malignant hyperthermia genetic diseases, thereby effectively preventing and treating malignant hyperthermia.

Further, the pharmaceutical composition for preventing or treating malignant hyperthermia of the present invention can be used even after the onset of malignant hyperthermia and can inhibit an abnormal oxygen consumption rate even at lower concentrations than those of conventional agents for treating malignant hyperthermia, thereby replacing conventional agents for treating malignant hyperthermia and can be stably used, thereby being effectively used in relevant industries.

Further, the skin regenerating composition of the present invention can protect the skin from skin cell damage induced by UV-B of ultraviolet rays. In addition, the skin regenerating composition of the present invention can be used as a skin external preparation, a pharmaceutical composition, a cosmetic composition, and a food composition, since it has excellent ability to recover and regenerate the skin from such damage and has no other side effects.

MODES OF THE INVENTION

The present invention provides a pharmaceutical composition for preventing or treating malignant hyperthermia comprising a NAADP antagonist.

As used herein, the term "nicotinic acid adenine dinucleotide phosphate (NAADP)" is derived from intracellular nicotinamide adenine dinucleotide phosphate (NADP) and is a cellular metabolite that plays a crucial role in cell signaling of various cells including those of liver, pancreas and muscle of human.

NAADP antagonists refer to compounds that are similar in structure to NAADP to bind to the receptor of NAADP but have little or no functional activity on their own for the receptor. In other words, NAADP antagonists can bind competitively against NAADP to receptors to which NAADP binds, thereby blocking the action of NAADP so that NAADP antagonists inhibit intracellular responses induced by NAADP.

As used herein, the term "prevention" means blocking the occurrence of the disease before the disease occurs, or finding the disease early and treating it timely.

As used herein, the term "treatment" includes not only cure of the disease, but also partial cure, improvement and alleviation of symptoms.

In the present invention, the NAADP antagonist is a compound having a structure represented by the following chemical formula 1.

[Chemical Formula 1]

Wherein X is halogen and R is OH or $OC_{1-5}$ alkyl.

As used herein, the term "halogen" means an element belonging to group 17 of the periodic table and includes F, Cl, Br, I and the like.

As used herein, the term "alkyl" refers to a monovalent substituent represented by the general formula $C_nH_{2n+1}$, in which $C_{1-5}$ alkyl refers to an alkyl having 1 to 5 carbon atoms. Specific examples of the substituent include methyl, ethyl, n-propyl, isopropyl, n-butyl, sec-butyl, isobutyl, tert-butyl, n-pentyl, tert-pentyl, neopentyl, isopentyl, sec-pentyl, and 3-pentyl.

Examples of the NAADP antagonist include NED-19, NED-20 and NED-19.4.

The NED-19 is a compound having a structure in which X=F and R=OH, and F is bonded in an ortho position in chemical formula 1.

The NED-20 is a compound having a structure in which X=F and R=OH, and F is bonded in a para position in chemical formula 1.

The NED-19.4 is a compound having a structure in which X=F and R=$OCH_3$, and F is bonded in an ortho position in chemical formula 1.

In the present invention, the malignant hyperthermia prevention and treatment is carried out by inhibiting the increase in the oxygen consumption rate.

The pharmaceutical composition for preventing or treating malignant hyperthermia of the present invention may lower the irreversible oxygen consumption rate in the skeletal muscle of a patient suffering from malignant hyperthermia genetic diseases, thereby preventing or treating malignant hyperthermia.

The pharmaceutical composition for preventing or treating malignant hyperthermia of the present invention may be used in combination with other conventional drugs used for the treatment of malignant hyperthermia. When used in combination with other conventional drugs, they can be administered sequentially or simultaneously, which can be readily determined by a person skilled in the art.

The present invention relates to a skin regenerating composition comprising at least one compound selected from the group consisting of the compounds represented by the above-described chemical formula 1 and the following chemical formula 2:

[Chemical Formula 2]

Wherein A is halogen, $NH_2$, $OC_{1-5}$ alkyl group or $C_{1-5}$ alkyl group; X is halogen and R is OH or $OC_{1-5}$ alkyl.

The compound represented by chemical formula 2 as described above may act as a cADPR antagonist.

cADPR antagonists refer to compounds that are similar in structure to cADPR to bind to the receptor of cADPR but have little or no functional activity on their own for the receptor. In other words, cADPR antagonists can bind competitively against cADPR to receptors to which cADPR binds, thereby blocking the action of cADPR so that cADPR antagonists inhibit intracellular responses induced by cADPR.

Examples of the cADPR antagonist include 8-Br-cADPR, 8-$NH_2$-cADPR, 8-$CH_3O$-cADPR, 8-$CH_3$-cADPR, and the like.

The 8-Br-cADPR has a structure in which X=Br in the chemical formula 1.

The 8-$NH_2$-cADPR has a structure in which X=$NH_2$ in the chemical formula 1.

The 8-$CH_3O$-cADPR has a structure in which X=$OCH_3$ in the chemical formula 1.

The 8-$CH_3$-cADPR has a structure in which X=$CH_3$ in the chemical formula 1.

The skin regenerating composition of the present invention may regenerate the skin by inhibiting the activity of IP3/NAADP/cADPR which is a secondary messenger.

The present invention provides a skin regenerating external preparation comprising the skin regenerating composition.

In the present invention, the skin regenerating external preparation can be formulated into a formulation selected from the group consisting of an external powder, an external solution, an ointment, a cream, a gel, a plaster, a dressing, a patch and a spray.

The skin external preparation of the present invention may further contain a pharmaceutically acceptable carrier, a diluent, an adjuvant, a coloring agent, a stabilizer, a flavor, a surfactant, an oil, a humectant, an alcohol, a thickening agent, an antioxidant, a pH adjusting agent, or a sunscreen so as to easily use and handle them within the scope of not impairing the skin regeneration effect of the present invention.

The present invention provides a skin disease-treating pharmaceutical composition comprising the skin regenerating composition.

In the present invention, the skin disease may be selected from the group consisting of keratosis, erythema nodosum, miliaria, pityriasis, strophulus, prurigo, and dermatitis.

The skin disease-treating pharmaceutical composition of the present invention may be used in combination with other conventional drugs used for the treatment of skin diseases.

When used in combination with other conventional drugs, they can be administered sequentially or simultaneously, which can be readily determined by a person skilled in the art.

The pharmaceutical composition of the present invention may be formulated into a formulation selected from the group consisting of a tablet, a granule, a pill, a capsule, a solution, an injection, an ointment, a suppository and a powder, but is not limited thereto.

The pharmaceutical composition of the present invention may include a carrier, an excipient and a diluent that can be generally included in a drug, and an available carrier, excipient and diluent include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinyl pyrrolidone, water, methylhydroxybenzoate, propylhydroxybenzoate, talc, magnesium stearate, and mineral oil.

When the pharmaceutical composition of the present invention is formulated, it may contain a filler, an extender, a binder, a wetting agent, a disintegrant, a surfactant and the like, which are commonly used. A solid preparation for oral administration includes a tablet, a pill, a powder, a granule, a capsule and the like. Such a solid preparation can be prepared by mixing at least one excipient such as starch, calcium carbonate, sucrose, lactose, gelatin and the like in the above extract. In addition to simple excipients, lubricants such as magnesium stearate and talc may also be used. A liquid preparation for oral administration includes suspensions, solutions, emulsions, syrups and the like. Various excipients such as a wetting agent, a sweetener, a fragrance, a preservative and the like may be included in addition to water and liquid paraffin, which are simple diluents commonly used. A preparation for parenteral administration includes a sterilized aqueous solution, a non-aqueous solution, a suspension, an emulsion, a freeze-dried preparation and a suppository. As a non-aqueous solution and suspension, propylene glycol, polyethylene glycol, vegetable oil such as olive oil, injectable ester such as ethyl oleate, and the like can be used. As a suppository base, witepsol, macrogol, tween 61, cacao paper, laurin, glycerogelatin and the like can be used.

The pharmaceutical composition of the present invention is administered in a pharmaceutically effective amount.

As used herein, the term "pharmaceutically effective amount" refers to an amount which is sufficient to treat a disease and a sufficiently low level of risk. Specific values may be determined according to factors including the kind and severity of the subject to be treated, age, sex, drug activity, sensitivity to drugs, administration time, administration route and release rate, treatment duration and co-administered drugs and other factors well known in the medical arts.

The administration route of the pharmaceutical composition of the present invention can be any general route so long as it can reach the target tissue. The composition of the present invention may be administered intraperitoneally, intravenously, intramuscularly, subcutaneously, intradermally, orally, intranasally, intrapulmonarily or rectally, but is not limited thereto. The composition may also be administered by any device capable of transferring the active agent to the target cell.

The present invention provides a cosmetic composition comprising the skin regenerating composition.

The cosmetic composition may additionally include typically added components, for example, a conventional additive and carrier such as an antioxidant, a stabilizer, a solubilizer, a vitamin, a pigment and fragrance.

The cosmetic composition may be prepared in any formulation conventionally produced in the art and may be prepared in the formation of, for example, a solution, a suspension, an emulsion, a paste, a gel, a cream, a lotion, a powder, a soap, a surfactant-containing cleansing, an oil, a powder foundation, an emulsion foundation, a wax foundation, and a spray, but is not limited thereto. More specifically, the cosmetic composition may be prepared in a formation of a cosmetic lotion such as a soft cosmetic lotion or a nutritional cosmetic lotion, a lotion such as a facial lotion and a body lotion, a cream such as a nutrition cream, a moisture cream and an eye cream, essence, a cosmetic ointment, a spray, a gel, a pack, a sunscreen, make-up base, a foundation such as a liquid-type foundation, a solid-type foundation or spray-type foundation, a powder, a make-up remover such as a cleansing cream, a cleansing lotion and a cleansing oil, and a detergent such as a cleansing foam, a soap, a body washer. In this case, the cosmetic composition may contain an excipient including a surfactant, an emulsifier, a soap acid, a solvent, a coloring agent, a preservative, an antioxidant, a defoamer, an antibacterial agent, an anti-redeposition agent, an enzyme, a plant or mineral oil, a fat, a fluorescent substance, a fungicide, a hydrotropic substance, a moisturizer, a flavoring agent, a flavoring agent carrier, a preservative, a protein, a silicone, a solubilizer, a sugar derivative, a sunscreen, a vitamin, a plant extract, a wax, and the like.

When the formulation of the cosmetic composition is a paste, a cream or a gel, an animal oil, a vegetable oil, a wax, paraffin, starch, tragacanth, a cellulose derivative, polyethylene glycol, silicone, bentonite, silica, talc or zinc oxide can be used as a carrier component.

When the formulation of the cosmetic composition is a powder or a spray, tose, talc, silica, aluminum hydroxide, calcium silicate or polyamide powder can be used as a carrier component. In particular, in the case of a spray, the carrier component may additionally include a propellant such as chlorofluorohydrocarbon, propane/butane or dimethyl ether.

When the formulation of the cosmetic composition is a solution or emulsion, a solvent, a solubilizer or an emulsifier is used as a carrier component, and examples thereof include water, ethanol, isopropanol, ethyl carbonate, ethyl acetate, benzyl alcohol, benzyl benzoate, propylene glycol, 1,3-butyl glycol oil, glycerol aliphatic ester or fatty acid esters of polyethylene glycol or sorbitan.

When the formulation of the cosmetic composition is a suspension, as the carrier component, a liquid diluent such as water, ethanol or propylene glycol, a suspension such as ethoxylated isostearyl alcohol, polyoxyethylene sorbitol ester and polyoxyethylene sorbitan ester, microcrystalline cellulose, aluminum metahydroxide, bentonite, agar or tragacanth, and the like can be used.

When the formulation of the cosmetic composition is a surfactant-containing cleansing, as the carrier component, aliphatic alcohol sulfate, aliphatic alcohol ether sulfate, sulfosuccinic acid monoester, isethionate, imidazolinium derivative, methyltaurate, sarcosinate, fatty acid amide ether sulfate, alkylamidobetaine, aliphatic alcohol, fatty acid glyceride, fatty acid diethanolamide, a vegetable oil, lanolin derivative, ethoxylated glycerol fatty acid ester and the like can be used.

The present invention provides a food composition comprising the skin regenerating composition.

The food composition may further include components typically added in the manufacture of the food, for example, a protein, a carbohydrate, a fat, a nutrient, a seasoning agent and a flavoring agent.

Examples of the carbohydrates include monosaccharides such as glucose and fructose; disaccharides such as maltose, sucrose and oligosaccharides; and polysaccharides such as normal saccharides such as dextrin, cyclodextrin and the like and sugar alcohols such as xylitol, sorbitol and erythritol. Natural flavorings such as taumartin and stevia extract (e.g., rebaudioside A, glycyrrhizin) and synthetic flavorings (saccharine, aspartame, etc.) can be used as flavoring agents.

EXPERIMENTAL EXAMPLE

Hereinafter, preferred Examples are described for the understanding of the present invention. However, the following Experimental examples are provided only for the purpose of easier understanding of the present invention, and the present invention is not limited by Experimental examples.

Experimental Outline of Therapeutic Effect of Malignant Hyperthermia

Malignant hyperthermia is a disease that occurs in patients with a genetic disorder of the ryanodine receptor (RYR) of the skeletal muscle and occurs in a patient with genetic defects of RYR1, the main RYR form of the skeletal muscle, when using an anesthetic. Although the patient's skeletal muscle may be directly examined at the tissue level through biopsy, such an examination method may invasively cause pain to the patient. Based on the fact in which RYR1 has the main RYR form in B cells from blood, unlike other immune cells (Sei et al., 1999), B cells from the blood of patients with malignant hyperthermia were collected, and experiments were conducted on an increase of oxygen consumption rate using an anesthetic.

Experimental Example 1 for the Therapeutic Effect of Malignant Hyperthermia: Isolation of B Cells Heparin-treated 5 mL of peripheral blood of patient and normal patient (WT) and RYR gene mutation patient (R2435H), respectively, were diluted 2-fold with RPMI 1640 and then overlaid on 3 mL of lymphoprep (Nyegaard, Oslo, Norway), and centrifuged at 2,000 rpm for 20 minutes by density gradient method to isolate peripheral blood mononuclear cells. The isolated cells were washed twice with RPMI 1640 (Sigma Co, USA) and then counted with a hemocytometer. Total $1 \times 10^5$ cells were stained with monoclonal antibodies, and then surface markers were analyzed by flow cytometry.

Experimental Example 2 for the Therapeutic Effect of Malignant Hyperthermia: Measurement of Oxygen Consumption Rate (% $O_2$) of B Cells The oxygen consumption rate of B cells was measured by using MITO-ID intracellular $O_2$ sensor probe (Enzo, ENZ-51046-K100, USA). 30,000 B cells were placed in a 96 well plate and maintained for 12 hours in a $CO_2$ incubator by using RPMI 1640 (Sigma Co, USA) in which MITO-ID probe was mixed at a ratio of 1:10. Then, the cells were treated with NED-19 and inducer such as caffeine, isoflurane, and halothane and the oxygen consumption rate was measured at 340/642 nm by using a fluorescence plate reader (Perkin Elmer, Envision, USA).

Figure 1:
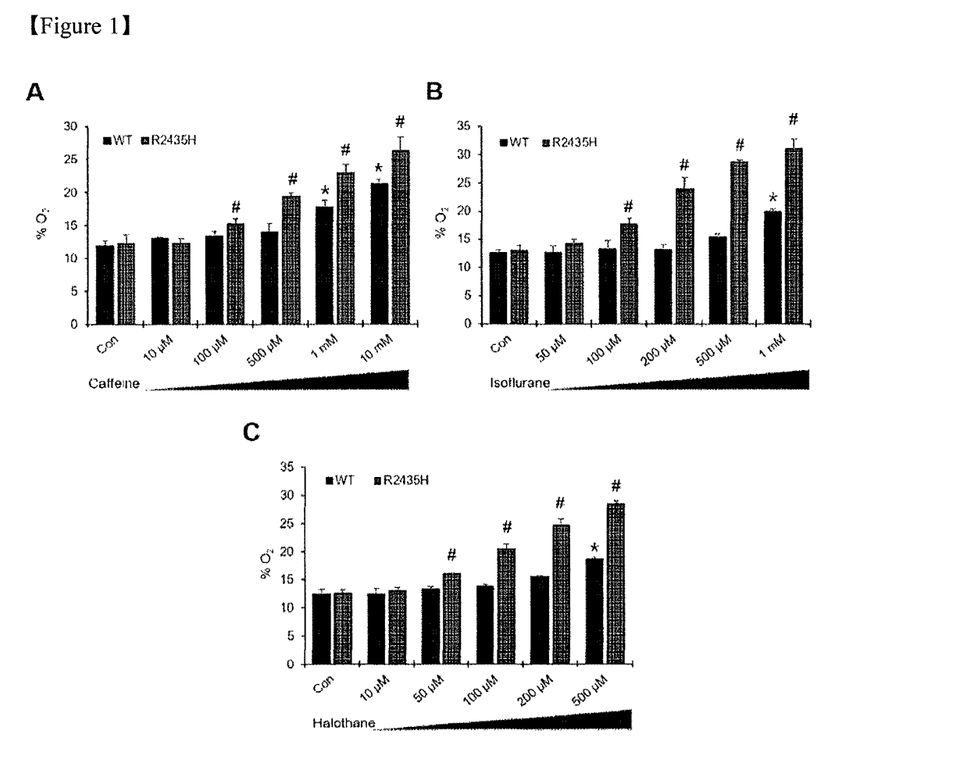
FIG. 1 shows changes of oxygen consumption rate (% $O_2$) in normal cells (WT) and RYR gene mutant cells (B2435H) showing a malignant hyperthermia response according to concentrations in caffeine (A), isoflurane (B) and halothane (C) treatment in human B cells with malignant hyperthermia (*, P<0.05 versus WT control (Con) level. #, P<0.05 versus R2435H Con level. One-way ANOVA. Error bars denote s.d.).

According to Hoppe et al. (2016), it has been reported that the oxygen consumption rate (% $O_2$) in the case of cells with malignant hyperthermia is significantly increased depending on the use of anesthetics, compared to normal cells. Specifically, B cells obtained from regular people and B cells obtained from patients with malignant hyperthermia were used to confirm abnormal increase in the oxygen consumption rate (% $O_2$) in B cells obtained from patients with malignant hyperthermia when induced by caffeine and anesthetics, showing a sensitive response to caffeine and inhalation anesthetics (isoflurane and halothane) treatment compared with normal cells. The results are shown in FIG. 1.

Figure 2:
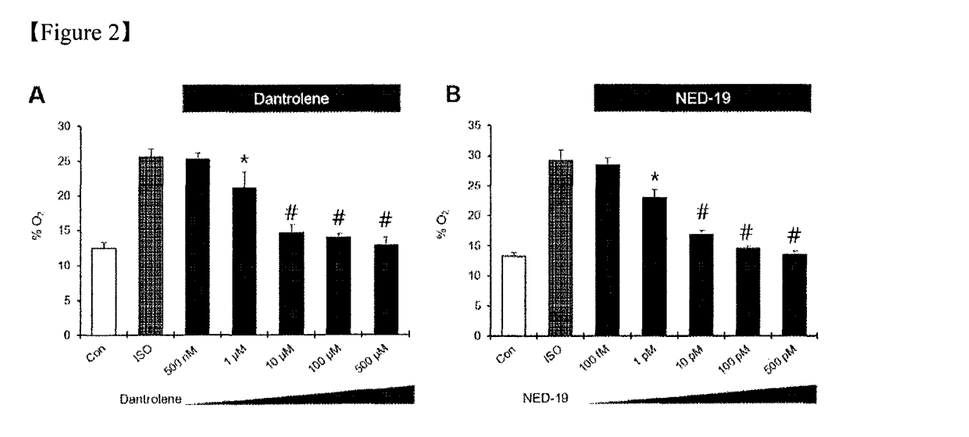
FIG. 2 shows changes of oxygen consumption rate (% $O_2$) in cells according to dantrolene and NED-19 treatment in RYR gene mutant cells (B2435H) showing a malignant hyperthermia response by isoflurane (ISO) treatment in human B cells with malignant hyperthermia (*, P<0.05 versus ISO treatment level. #, P<0.01 versus ISO treatment level. One-way ANOVA. Error bars denote s.d.).

Considering the fact that dantrolene was used clinically for the treatment of malignant hyperthermia, the inhibitory effects of NED-19 on malignant hyperthermia was compared to those of dantrolene. When dantrolene was applied to cells with malignant hyperthermia, the inhibitory effect was observed at a concentration of about 10 μM, whereas NED-19 showed an inhibitory effect even at a low concentration of 10 pM to 100 pM. The results indicate that NED-19 was more effective at lower concentrations. The results are shown in FIG. 2.

Figure 3:
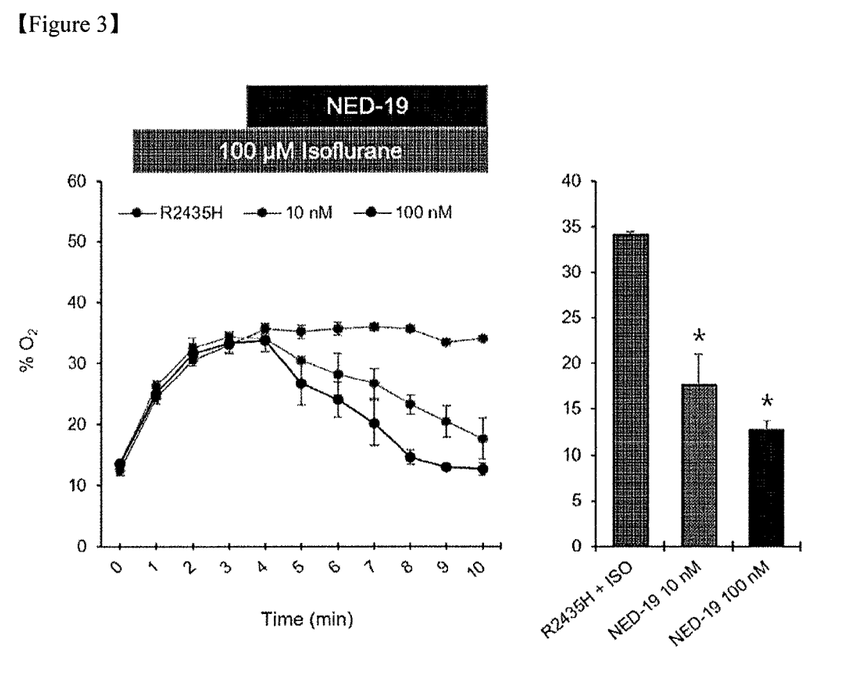
FIG. 3 shows effects of inhibiting oxygen consumption rate (% $O_2$) in cells according to NED-19 treatment after the malignant hyperthermia response induced by isoflurane (ISO) treatment in human B cells (B2435H) with malignant hyperthermia (*, P<0.05 versus ISO treatment level. One-way ANOVA. Error bars denote s.d.).

In addition, after inducing malignant hyperthermia with isoflurane in the RYR gene mutant cells (R2435H), the cells were post-treated with 10 nM to 100 nM NED-19. The results indicate that the increase of the oxygen consumption rate was stably inhibited even after post-treating malignant hyperthermia-induced cells (R2435H) with NED-19. The results are shown in FIG. 3.

Experimental Example 1 for Skin Regeneration Effect: Test of Inhibition Ability of Isolation of IL-1β Induced by UV-B of 8-Br-cADPR and Ned-19

Figure 4:
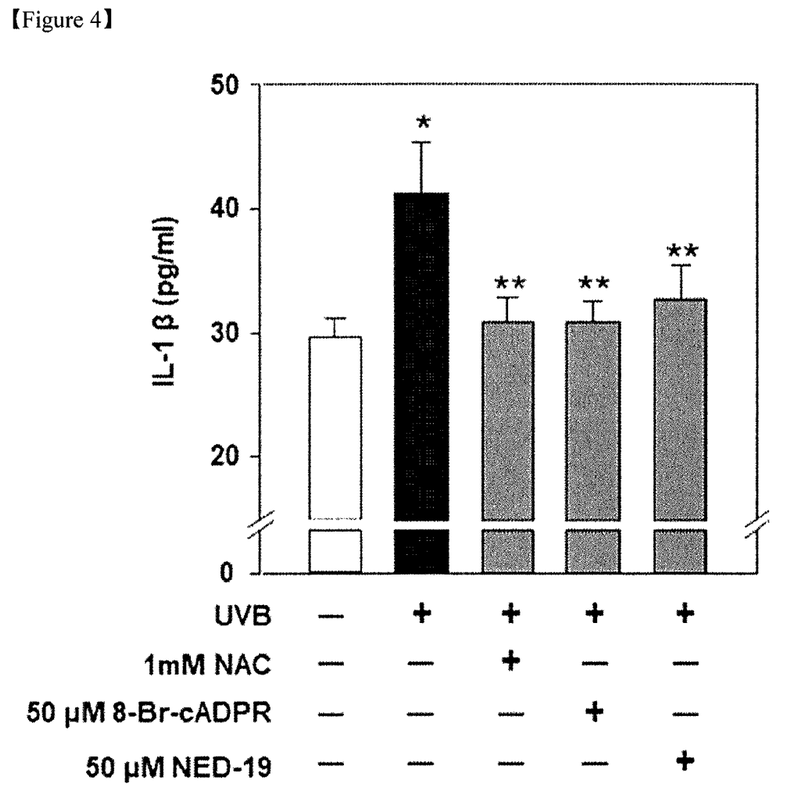
FIG. 4 shows the results of verifying the improved efficacy by applying 8-Br-cADPR and NED-19 to damage models of UV-B induced human epithelial keratinocytes (HEKn cells) and measuring the isolation amount of IL-1β.

The effect of the present invention was confirmed by quantifying the amount of IL-1β, which is a typical inflammatory factor released in the culture supernatant of human epithelial keratinocytes (HEKn cells, ATCC, USA) irradiated under normal conditions or UV-B, respectively. The results are shown in FIG. 4. 8-Br-cADPR and Ned-19 were pre-treated for 20 minutes at a concentration shown in FIG. 4 and then irradiated with 50 mJ of UV-B. The culture solution of the cells further cultured for 12 hours to 24 hours in a carbon dioxide incubator was collected and centrifuged at 15,000 rpm for 20 minutes at 4° C., and the supernatant was used as a sample. The isolated IL-1β was measured by using a commercialized quantitation kit (R&D Systems, USA) according to the supplier's manual.

Experimental Example 2 for Skin Regeneration Effect: Verification of Skin Regeneration Using 8-Br-cADPR and Ned-19

Figure 5:
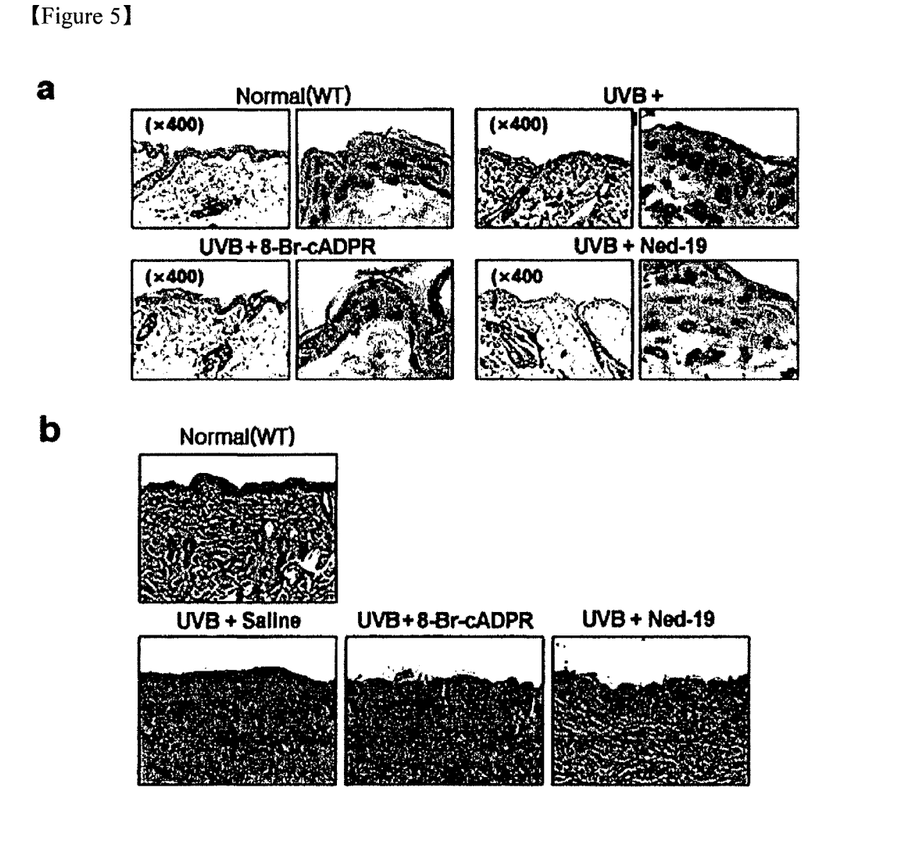
FIG. 5 shows the result of confirming skin damage inhibitory effects and regeneration effects by applying 8-Br-cADPR and NED-19 to damage models of UV-B induced skin and performing H & E staining.

It was confirmed that the primary intracellular injury mechanism induced by ultraviolet ray UV-B in human epidermal keratinocytes (HEKn) was caused by the second messenger, IP3/NAADP/cADPR. Accordingly, 8-Br-cADPR and Ned-19 were applied to skin damage model induced by ultraviolet ray UV-B. The results indicate that skin damage was effectively inhibited, and skin regeneration was promoted. The results are shown in FIG. 5.

What is claimed is:

1. A method of treating malignant hyperthermia comprising administering an effective amount of a compound represented by the following chemical formula 1 to an individual in need thereof:

Chemical Formula 1 wherein X is halogen and R is OH or OC$_{1-5}$ alkyl.

2. The method of claim 1, wherein X is F which is bonded in ortho or para position.

3. The method of claim 1, wherein R is OH or OCH$_3$.

4. The method of claim 1, wherein the compound has a structure represented by the following chemical formula 3:

Chemical Formula 3

* * * * *